(12) United States Patent
Doguet et al.

(10) Patent No.: US 12,263,344 B2
(45) Date of Patent: Apr. 1, 2025

(54) CONTROL SYSTEM FOR AN IMPLANTABLE STIMULATING DEVICE FOR STIMULATING A VAGUS NERVE

(71) Applicant: Synergia Medical, Mont-Saint-Guibert (BE)

(72) Inventors: Pascal Doguet, Mont-Saint-Guibert (BE); Marie Dautrebande, Mont-Saint-Guibert (BE); Yohan Botquin, Mont-Saint-Guibert (BE); Gregory Thiebaut, Mont-Saint-Guibert (BE)

(73) Assignee: Synergia Medical, Mont-Saint-Guibert (BE)

( * ) Notice: Subject to any disclaimer, the term of this patent is extended or adjusted under 35 U.S.C. 154(b) by 655 days.

(21) Appl. No.: 17/312,489

(22) PCT Filed: Dec. 18, 2018

(86) PCT No.: PCT/EP2018/085485
§ 371 (c)(1),
(2) Date: Jun. 10, 2021

(87) PCT Pub. No.: WO2020/125948
PCT Pub. Date: Jun. 25, 2020

(65) Prior Publication Data
US 2022/0054841 A1 Feb. 24, 2022

(51) Int. Cl.
*A61N 1/372* (2006.01)
*A61N 1/05* (2006.01)
(Continued)

(52) U.S. Cl.
CPC ....... *A61N 1/36139* (2013.01); *A61N 1/0556* (2013.01); *A61N 1/36053* (2013.01);
(Continued)

(58) Field of Classification Search
CPC ............ A61N 1/36053; A61N 1/36114; A61N 1/36128; A61N 1/36142
See application file for complete search history.

(56) References Cited

U.S. PATENT DOCUMENTS

| 2011/0313483 A1 | 12/2011 | Hincapie Ordonez et al. |
| 2012/0271382 A1 | 10/2012 | Arcot-Krishnamurthy et al. |

(Continued)

FOREIGN PATENT DOCUMENTS

WO     2016131492 A1     8/2016

OTHER PUBLICATIONS

Int'l Search Report for PCT/EP2018/085485, dated Nov. 4, 2019.

*Primary Examiner* — Allen Porter
(74) *Attorney, Agent, or Firm* — MaxGoLaw PLLC

(57) ABSTRACT

A kit of parts and method for the control of a delivery of an electric or electromagnetic pulse to a vagus nerve by an implanted stimulating device is provided. The kit of parts includes an implantable stimulating device (10) that includes a cuff electrode/optrode for being coupled to a vagus nerve (Vn) of a patient to be treated, and an encapsulation unit (50) suitable for being subcutaneously implanted at a location separated from the vagus nerve coupling unit (60), and enclosing an energy pulse generator (51s), for delivering electrical or optical energy pulses, and coupled to the cuff electrode/optrode by one or more electrical conductors (41e) and/or optical fibres (41f), an external controller device (100) of the kit includes laryngeal electrodes (161) suitable for being coupled to a laryngeal region (Lx) of a patient for measuring a laryngeal electrical activity at the laryngeal region, the laryngeal electrodes being coupled to an external control unit (150). The unit includes (Continued)

a setting unit (151) for entering control pulse parameters of a control energy pulse an external emitter (153*e*) configured for sending a signal to the implanted controller (54) to deliver to the cuff electrode/optrode one or more control energy pulses defined by the control pulse parameters entered in the setting unit, and a visual (155) or acoustic (157) display indicative of the intensity of the laryngeal electrical activity.

14 Claims, 6 Drawing Sheets

(51) Int. Cl.
*A61N 1/36* (2006.01)
*A61N 5/06* (2006.01)

(52) U.S. Cl.
CPC ..... *A61N 1/36167* (2013.01); *A61N 1/37247* (2013.01); *A61N 5/0622* (2013.01); *A61N 2005/0626* (2013.01); *A61N 2005/063* (2013.01); *A61N 2005/0651* (2013.01)

(56) References Cited

U.S. PATENT DOCUMENTS

| | | |
|---|---|---|
| 2013/0053926 A1 | 2/2013 | Hincapie Ordonez et al. |
| 2013/0245486 A1 | 9/2013 | Simon et al. |
| 2016/0151628 A1* | 6/2016 | Simon ................ A61B 5/4836 607/2 |

* cited by examiner

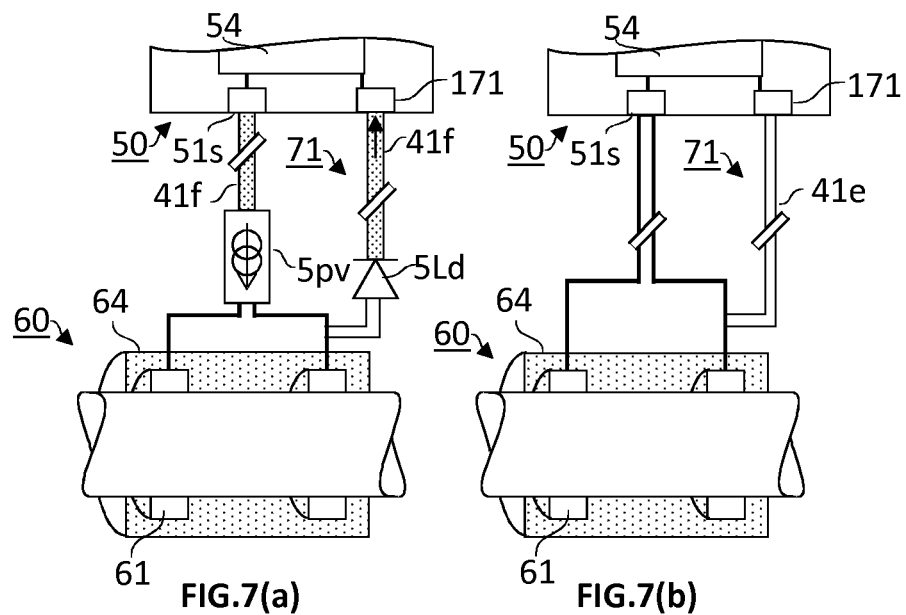
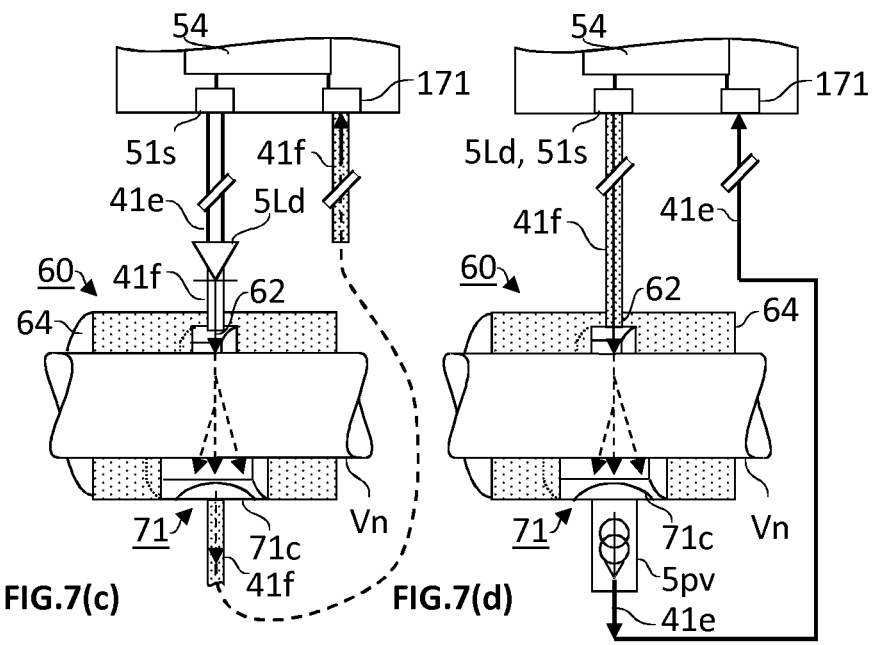

CONTROL SYSTEM FOR AN IMPLANTABLE STIMULATING DEVICE FOR STIMULATING A VAGUS NERVE

TECHNICAL FIELD

The present invention is in the field of active implantable medical devices (AIMD) for use in medical treatments involving the transmission of electrical pulses or light pulses (=energy pulses) between an energy pulse generator enclosed in an encapsulation unit and a vagus nerve. More particularly, the present invention concerns a kit of parts and a method for determining a satisfactory set of control parameters of energy pulses ensuring that the vagus nerve is effectively activated by such energy pulses. Once a satisfactory set of control parameters has been determined, a therapeutic set of parameters can be derived from the satisfactory set of control parameters. The present invention comprises an external controller device capable of communicating with an implanted medical device, the external controller device comprising a laryngeal electrode unit capable of recording an electrical activity of a laryngeal region following the delivery to the vagus nerve of a control stimulation pulse.

BACKGROUND OF THE INVENTION

Active implantable medical devices (AIMD) have been used for decades for treating a number of disorders, in particular neurological disorders. A type of AIMD's consists of neurostimulators, which deliver electrical pulses to nerves, such as the vagus nerve, for treating a number of neurological disorders such as epilepsy, Crohn disease, obesity, Parkinson's disease, and even depression. An AIMD for stimulating a vagus nerve generally comprises a vagus nerve coupling unit adapted for coupling electrodes (61) or an optrode (62) to the vagus nerve. The delivery of energy pulses requires an energy pulse generator, powered by a source of power, and controlled by an implanted controller. Because of their size, it is generally not possible to lodge all these components in close proximity to a vagus nerve coupling location. For this reason stimulating implants are generally split into two separate components: on the one hand, the electrodes or optrodes which are included in the vagus nerve coupling unit (60), and implanted and coupled directly to the vagus nerve and, on the other hand, the energy (electrical or light) pulse generator (51*s*) encapsulated in a housing (50*h*), which can be implanted at a distance from the vagus nerve, often in the subclavian region. The transfer of energy between the energy pulse generator and the vagus nerve coupling unit is ensured by electrical conductors (41*e*) for conducting electrical energy, or by optical fibres (41*f*) for transporting optical energy.

A nerve typically consists of a bundle of nerve fibres. A nerve is activated by a stimulation pulse if at least one of its nerve fibres triggers an action potential, which propagates along its length. An action potential is triggered by a local depolarisation of the membrane of the nerve fibre. The membrane potential rapidly rises and falls causing adjacent locations to similarly depolarise. This depolarisation then propagates along the nerve fibre. When several nerve fibres are activated, the sum of all these action potentials that propagate within the nerve is called a compound action potential.

An activation threshold is defined as a set of parameters values defining a stimulation pulse, wherein a nerve is activated for all values of any parameter of said set which are greater than or equal to the threshold value of the corresponding parameter, and wherein the nerve is not activated for all values of any parameter of said set which are lower than the threshold value of the corresponding parameter.

As illustrated in FIG. 1, the present invention concerns AIMD's comprising:
- an encapsulation unit (50) including a housing (50*h*) enclosing a source of power (52), any analog and/or digital circuit referred to as an implanted controller (54), and an energy pulse generator, (51*s*), for generating electrical pulses, either current or voltage controlled, or pulses of light,
- a vagus nerve coupling unit (60) comprising one or more electrodes and/or optrodes suitable for being implanted and coupled directly onto the vagus nerve, and
- an implanted energy transfer unit (41) comprising one or more electrical conductors (41*e*) and/or optical fibres (41*f*) for transferring energy pulses between the encapsulation unit and the vagus nerve coupling unit.

In its simplest form, an encapsulation unit (50) for delivering energy pulses to a vagus nerve coupling unit (60) generally comprises an energy pulse generator (51*s*) powered by a source of power (52), such as a battery, and an implanted controller (54) for controlling a set of parameters of the energy pulses to be delivered by the energy pulse generator, including but not limited to, intensity (I1, I2), duration (d1, d2), number (N), and frequency (f1, f2) of deliveries, shape of the pulses, etc. The foregoing elements are lodged in a housing (50*h*) (cf. FIG. 2(*a*)&2(*b*)).

The vagus nerve coupling unit (60) is generally in the form of a cuff electrode or optrode, comprising an insulating support sheet shaped as a cylindrical cuff wrapping a portion of the vagus nerve (Vn). Two electrodes (61) separated from one another can be arranged at an inner surface of the cylindrical cuff, forming an electrical circuit with the vagus nerve when the insulating support sheet is wrapped around the vagus nerve. A third electrode can be provided to reduce stray currents and concentrate the current within the portion of vagus nerve wrapped by the cuff electrode.

In recent years, treatment of tissues with optical energy has shown encouraging potential for the treatment of disorders, either to support the field of optogenetics or using direct infrared light. For such light treatments of a tissue, a so-called optrode (62) can be used. An optrode can be a light emitter focusing a light beam onto a precise area of a tissue, or it can be a light sensor, sensing a reflected, transmitted, or scattered light beam emitted by a light emitter. The light emitter can be powered by electric current in a similar way as the electrodes discussed supra. The optrode can be coupled to the insulating support sheet facing an opening allowing optical contact with the vagus nerve when the cuff optrode is wrapped around the vagus nerve.

The implantation of an AIMD includes the following steps. A surgeon opens the area comprising the vagus nerve and couples the vagus nerve coupling unit to the vagus nerve. The vagus nerve coupling unit is generally electrically or optically coupled to the distal end of an implanted energy transfer unit (41) comprising one or more electrical conductors and/or optical fibres before implanting the vagus nerve coupling unit to the vagus nerve. A proximal end of the implanted energy transfer unit is driven to the location of implantation of the encapsulation unit, such as in the subclavian region. The encapsulation unit can be implanted and coupled to the implanted energy transfer unit in any sequence.

About one third of the patients treated for epilepsy by vagus nerve stimulations are non-respondent to the therapy. Within this third of patients, however, it must be distinguished between the patients whose vagus nerve is activated but does not yield the desired cure, and the patients whose vagus nerve has not been activated because of a deficiency in the AIMD device, a non-optimal implantation operation, a set of parameters below the activation threshold, or because the vagus nerve is damaged.

Once implanted, it must be ensured that the energy pulses generated by the implanted AIMD and transported to the vagus nerve do activate the vagus nerve according to a desired therapeutic plan. For example, depending on the implanting conditions, energy pulses (V1) of a first intensity may be too low for sufficiently activating the vagus nerve. A patient having an implanted AIMD programmed for delivering energy pulses (V1) of first intensity would therefore not be satisfactorily treated and the invasive operation required for the implantation of the AIMD would have been useless. A vagus nerve can also fail to be activated in spite of a successful delivery thereto of an energy pulse because it is injured or damaged.

By contrast, if the AIMD is programmed for delivering energy pulses of an intensity excessively above an intensity activation threshold of the vagus nerve, not only excessive energy is consumed, thus reducing the lifetime of the implanted battery but also it increases the risk of damaging the nerve.

For example, U.S. Pat. No. 6,266,558 proposes for determining an activation of a nerve electrically stimulated by an AIMD to detect at least two sequential evoked signals from the nerve or from a muscle innervated by said nerve in response to the stimulus.

U.S. Pat. No. 7,561,918 proposes to implant a sensing electrode on the vagus nerve to detect an electrical activity of the vagus nerve following the delivery of an electrical energy pulse to the vagus nerve between two stimulating electrodes. The stimulation feedback is, however, restricted to the portion of vagus nerve located in the direct neighbourhood of the vagus nerve coupling unit.

US2008058874 and US2010324628 describe a method for indirectly monitoring the neural stimulation of the vagus nerve by an AIMD, by recording the laryngeal activity provoked by said neural stimulation. The laryngeal activity includes the magnitude and frequency of the vibration of the larynx and provides for an indication of whether the vagus nerve is activated by neural stimulation. The recording of the laryngeal activity can be carried out with an accelerometer.

The present invention proposes a device and a method for monitoring the activation of the vagus nerve upon stimulation thereof by delivery of an electric or electromagnetic pulse by an implanted stimulating device. The device and method of the present invention allows the determination of a satisfactory set of control parameters. A therapeutic set of parameters can be defined from this satisfactory set of control parameters, for implementing a therapeutic plan for a given patient. The device and method of the present invention are simple to implement, and the results are highly reliable and reproducible. These and other advantages are described in more details in the following sections.

SUMMARY OF THE INVENTION

The present invention is defined in the appended independent claims. Preferred embodiments are defined in the dependent claims. In particular, the present invention concerns a kit of parts for the control of a delivery of an electric or electromagnetic pulse to a vagus nerve by an implanted stimulating device, said kit of parts comprising:
  (a) An implantable stimulating device comprising;
    A vagus nerve coupling unit comprising electrodes (61) and/or an optrode mounted on an insulating support forming a tubular cuff suitable for being coupled directly to a vagus nerve of a patient to be treated,
    an encapsulation unit suitable for being subcutaneously implanted at a location separated from the vagus nerve coupling unit, and comprising a housing enclosing,
      an energy pulse generator, for delivering energy pulses including electrical or optical energy,
      a source of power for activating the energy pulse generator,
      an implanted controller configured for instructing the external control unit to deliver energy pulses to the vagus nerve coupling unit, and
      an implanted receiver for receiving signals from an external emitter,
    an implanted energy transfer unit comprising one or more electrical conductors and/or optical fibres for transferring electrical and/or optical energy between the energy pulse generator of the encapsulation unit and the vagus nerve coupling unit,
  (b) An external controller device comprising;
    A laryngeal electrode unit comprising laryngeal electrodes suitable for being coupled to a skin of a neck of a patient at the level of a laryngeal region and suitable for measuring a laryngeal electrical activity at the laryngeal region,
    An external energy transfer unit comprising one or more electrical conductors or optical fibres for transferring an electrical or optical signal from the laryngeal electrode unit to an external control unit or to an intermediate controller in communication with the external control unit, said electrical or optical signal being representative of a laryngeal electrical activity measured at the laryngeal region, wherein
    the external control unit comprises,
      a setting unit for entering control pulse parameters of a control energy pulse
      an external emitter configured for sending a signal to the implanted receiver instructing the implanted controller to instruct the energy pulse generator to deliver to the vagus nerve coupling unit one or more control energy pulses defined by the control pulse parameters entered in the setting unit, and
      a converter converting electrical or optical signals transferred by the external energy transfer unit into a visual or acoustic display indicative of the intensity of the electrical or optical signal.

It is preferred that the implanted controller comprises an implanted emitter for sending a signal to the external control unit informing that a control energy pulse has been delivered by the energy pulse generator. The external control unit,
  is configured for saving a trigger time, t0, representative of the time, tv, a control energy pulse was delivered to the vagus nerve, wherein t0 is the time the signal was sent by the external emitter to the implanted receiver to deliver one or more control energy pulses,
  comprises an external receiver for receiving signals sent by the implanted emitter, and for saving a delivery signal time, td, representative of a delivery time, tv, a control energy pulse was delivered to the vagus nerve, wherein td is preferably the time the external receiver received the signal sent by the implanted emitter.

In a preferred embodiment, the vagus nerve coupling unit comprises a pulse feedback unit activated by electrical current flowing between two electrodes or by light emitted by an optrode of the vagus nerve coupling unit. The implanted energy transfer unit can comprise an electrical conductor or an optical fibre for transferring electrical or optical energy from the pulse feedback unit to a feedback sensor enclosed in the encapsulation unit and coupled to the implanted controller. The implanted controller can be coupled to an implanted emitter for sending a signal to the external control unit informing that the pulse feedback unit has been activated. Finally, the external control unit can comprise an external receiver for receiving the signal sent by the implanted emitter and can be configured for saving a delivery signal time, td, representative of the actual delivery time, tv, a control energy pulse was actually delivered to the vagus nerve.

In a preferred example of realization of the foregoing embodiment, the vagus nerve coupling unit comprises electrodes and the pulse feedback unit comprises a feedback electrical circuit connected to the feedback sensor either by an electrical conductor or by an optical fibre coupled to a light emitting diode (LED).

In another example of realization, the vagus nerve coupling unit comprises at least an optrode and the pulse feedback unit comprises a light collector for receiving light energy transmitted or scattered through the tissue. The light collector is connected to the implanted controller either by an electrical conductor coupled to a photovoltaic cell, or directly by an optical fibre.

The vagus nerve coupling unit can comprises a bipolar electrode including two electrodes or, preferably a tripolar electrode including three electrodes, separated from one another and exposed to an inner surface of the insulating sheet.

The kit of parts of the present invention may further comprise, a device for measuring an electrocardiogram of the patient coupled to the external control unit. The external control unit may be configured for synchronizing the sending of the signal to deliver to the vagus nerve coupling unit one or more control energy pulses such that a time, tlx, at which a laryngeal electrical activity (L1, L2) is expected corresponds to an isoelectric period of the electrocardiogram.

The present invention also concerns a method for adjusting the parameters of an implanted stimulating device coupled to a vagus nerve of a patient, comprising the following steps,
(a) providing a patient having an implantable stimulating device (10) as defined supra implanted in its body, with the vagus nerve coupling unit coupled to a vagus nerve of the patient,
(b) providing an external controller device as defined supra, and coupling the laryngeal electrode unit to a skin of the patient in the laryngeal region,
(c) entering a set of control parameters defining a control energy pulse into the setting unit,
(d) sending through the external emitter a signal to the implanted receiver instructing the energy pulse generator to deliver to the vagus nerve coupling unit one or more control energy pulses as defined by the set of control parameters,
(e) defining a trigger time, t0, representative of a time at which a control energy pulse was delivered to the vagus nerve, wherein t0 is defined as the time the signal was sent by the external emitter to the implanted receiver to deliver one or more control energy pulses,
(f) controlling whether the laryngeal electrode unit records a laryngeal electrical activity delayed from the trigger time by a predefined control time range, $\Delta t \pm \delta t$, with $\delta t < \Delta t$.

If no laryngeal electrical activity attributed to the energy pulse is recorded within the propagation time range, $\Delta t \pm \delta t$, a second set of control parameters defining a second control energy pulse can be entered into the setting unit, and steps (d) to (f) can be repeated with the second set of control parameters.

When, on the other hand, a laryngeal electrical activity is recorded within the propagation time range, $\Delta t \pm \delta t$, said laryngeal electrical activity can be compared with a predefined criterion of satisfaction.

If the laryngeal electrical activity thus recorded does not fulfil the predefined criterion, then a new set of control parameters defining a new control energy pulse can be entered into the setting unit, and steps (d) to (f) can be repeated with the new set of parameters.

If the laryngeal electrical activity thus recorded fulfils the predefined criterion, then the corresponding set of control parameters of the control energy pulse can be transmitted to the implanted controller for saving it as a satisfactory set of control parameters of an energy pulse. A therapeutic set of parameters can then be defined on the basis of the satisfactory set of control parameters to implement a predefined therapeutic plan.

A set of control parameters can include one or more of a pulse frequency, a pulse amplitude, a pulse duration, a pulse interval, a pulse number.

After step (c) a given set of control parameters can be saved in a memory to form a set of saved control parameters, and step (d) can be repeated sequentially several times instructing the energy pulse generator to deliver to the vagus nerve coupling unit (60) control energy pulses as defined by the set of saved control parameters.

Step (d) can be repeated sequentially N times instructing the energy pulse generator to deliver to the vagus nerve coupling unit one or more control energy pulses as defined by a given set of control parameters. The laryngeal electrical activity recorded by the laryngeal electrode unit can be averaged over the N repetitions of step (f), wherein N is a natural number greater than 1, to increase the signal to noise ratio.

In a preferred embodiment, an electrocardiogram of the patient is measured and the delivery to the vagus nerve coupling unit (60) of one or more control energy pulses is synchronized to correspond to an isoelectric period of a cardiac cycle of the patient.

BRIEF DESCRIPTION OF THE FIGURES

For a fuller understanding of the nature of the present invention, reference is made to the following detailed description taken in conjunction with the accompanying drawings in which:

FIG. 7: shows four embodiments of feedback units, (a)&(b) associated with a cuff electrode and (c)&(d) associated with a cuff optrode.

DETAILED DESCRIPTION OF THE INVENTION

The kit of parts of the present invention comprises
an active implantable stimulating device (AIMD) (10) for being implanted in a patient and coupled to a vagus nerve and
an external controller (100) in communication with the AIMD for assessing whether energy pulses delivered by the AIMD have activated the vagus nerve.

Figure 1A:
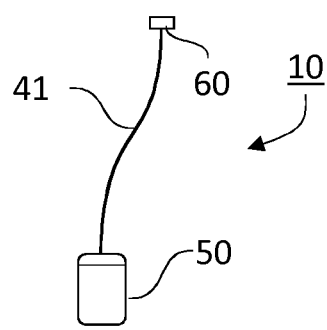
FIG. 1: shows (a) an AIMD and (b) an external controller device, both suitable to the present invention.
Figure 1B:
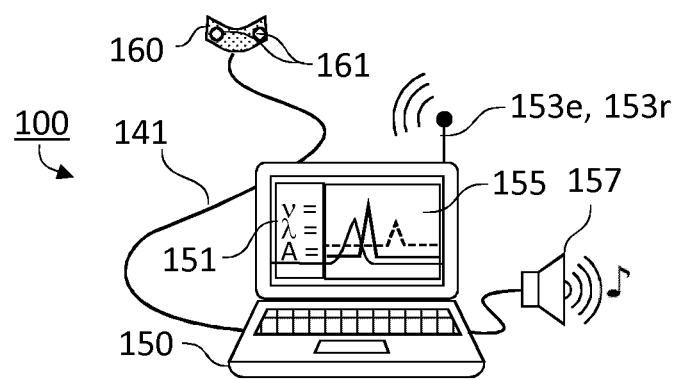

FIG. 1(a) illustrates an active implantable medical devices (AIMD) comprising,
A vagus nerve coupling unit (60) comprising electrodes (61) and/or optrodes (62) mounted on an insulating sheet (64) forming a cuff suitable for being coupled directly to a vagus nerve (Vn) of a patient;
an encapsulation unit (50) suitable for being subcutaneously implanted at a location separated from the vagus nerve coupling unit (60); and enclosing an energy pulse generator (51s) for delivering energy pulses including electrical or optical energy,
an implanted energy transfer unit (41) comprising one or more electrical conductors (41e) (e.g., conductive wires) and/or optical fibres (41f) for transferring electrical and/or optical energy between the energy pulse generator (51s) of the encapsulation unit and the vagus nerve coupling unit (60), FIG. 1(b) illustrates an external controller device (100) comprising,
a laryngeal electrode unit (160) comprising laryngeal electrodes (161) suitable for being coupled to a skin of a neck of a patient at the level of a laryngeal region (Lx) and suitable for measuring a laryngeal electrical activity at the laryngeal region;
an external control unit (150) coupled to the laryngeal electrode unit by
an external energy transfer unit (141) comprising one or more electrical conductors or optical fibres for transferring an electrical or optical signal from the laryngeal electrode unit to the external control unit (150).

AIMD: Encapsulating Unit of the AIMD

Figure 2A:
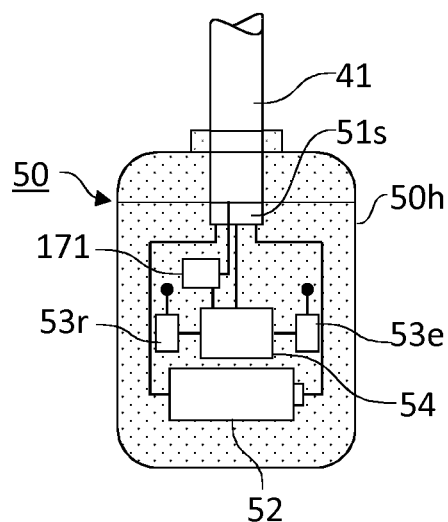
FIG. 2: shows (a) an encapsulation unit suitable for the present invention and (b) examples of energy pulses generated by the energy pulse generator.
Figure 2B:
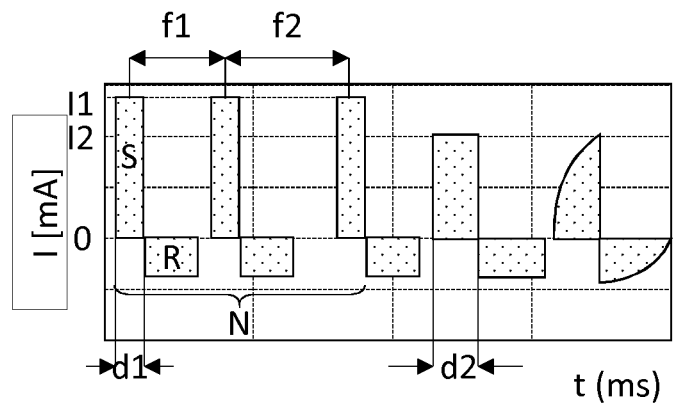

As illustrated in FIG. 2(a), the encapsulation unit (50) is formed by a housing (50h) defining an inner space enclosing an energy pulse generator (51s). The energy pulse generator can generate electrical pulses or light pulses, preferably in a wavelength ranging between 350 and 1650 nm. The energy pulses can have any shape (e.g., as illustrated in FIG. 2(b)) and can even comprise a train of repeated individual energy pulses. The energy pulses are characterized by a set of parameters, including intensity, (I1, I2), frequency (f1, f2), duration (d1, d2), number (N), shape, and the like. A typical set of parameters for electrical stimulation of the vagus nerve includes intensities (I1, I2) lower than 3.5 mA, at a frequency (f1, f2) comprised between 1 and 30 Hz, and durations (d1, d2) comprised between 100 and 1000 μs. Pulses can be generated by trains of duration comprised between 5 s and 5 min. Two trains of pulses can be separated by off-periods of 0.1 to 60 min. These values are illustrative only, and other values can be decided by a practitioner.

As can be seen in FIG. 2(b), each electrical stimulation pulse (S) generated by the energy pulse generator (51s) is usually followed by a recovery pulse (R) having same energy (same area under the curve) as, and of opposite sign to the stimulation pulse (S), and of lower intensity (in absolute values) than the intensity activation threshold value. The recovery pulses (R) permit the neutralization of any charges building up in the tissues following an electrical stimulation pulse (S). The present invention is not restricted to any one of the foregoing parameters and allows assessing whether an energy pulse defined by a given set of parameters yields a satisfactory activation of the vagus nerve. It also allows a therapeutic set of parameters to be determined to match a given therapeutic plan on a given patient having a given AIMD implanted and coupled to its vagus nerve.

The housing (50h) also encloses a source of power (52). The source of power is preferably in the form of a battery, preferably a rechargeable battery. An example of system for charging a rechargeable battery enclosed in the housing of an implanted medical device is described in EP3265173. The source of power is coupled to the energy pulse generator (51s) and supplies the power needed for the delivery of energy pulses. The source of power also supplies power to an implanted controller (54).

AIMD: Implanted Controller (54)

The implanted controller (54) has multiple functions. First, it controls the energy pulse generator for delivering energy pulses to the vagus nerve coupling unit according to a given set of parameters. The given set of parameters can be pre-programmed into the implanted controller prior to implanting the encapsulation unit. According to the present invention, however, the implanted controller can communicate with the exterior by means of an implanted receiver (53r) for receiving signals from an external emitter (153e).

The implanted controller is preferably also able to emit information to an external receiver (153r) by means of an implanted emitter (53e). The implanted emitter (53e) and receiver (53r) can be two separate units or can be merged in a single transceiver able to send and receive information. This way, the implanted controller can be instructed from an external emitter to order the energy pulse generator (51s) to deliver energy pulses according to a given set of parameters. The energy pulses can be control energy pulses, for assessing the good functioning of the AIMD, or can be therapeutic energy pulses for treating a disease like epilepsy, Crohn disease, depression, obesity, and the like. Similarly, the implanted controller (54) can emit feedback information to an external receiver, including for example, that a given pulse has been delivered, or that a feedback signal had been received from the vagus nerve coupling unit (60). Communication between an implanted emitter/receiver and an external receiver/emitter can be carried out by transmission of electromagnetic waves including infrared, visible or UV light, or radio-frequency. Radio frequencies can travel across tissues, fat and skin of a patient. Light can be transmitted through tissues, fat, and skin of a patient, provided the tissues to be traversed are not too thick (e.g., less than 10 mm thick, preferably less than 5 mm thick).

Figure 6:
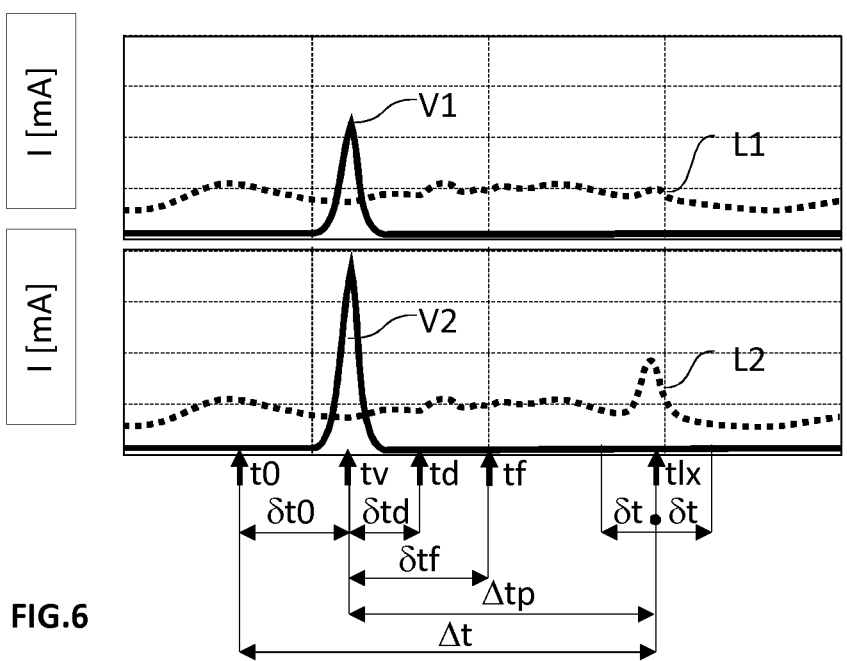
FIG. 6: shows the electrical laryngeal activity (dotted lines) following an energy stimulation by an energy pulse V1 and V2 (solid lines). The electrical laryngeal activity L1 cannot be distinguished from the noise, whilst the electrical laryngeal activity L2 can clearly be distinguished after a time period Δt.

As discussed supra, in a preferred embodiment, the implanted controller can receive a signal from an external emitter to deliver a control pulse defined by a given set of parameters. It can also emit a signal to an external receiver that the pulses have been delivered by the energy pulse generator (51s). Referring to FIG. 6 (solid line), a control energy pulse (V1, V2) can be delivered to the vagus nerve coupling unit (60). A peak shaped signal is represented in FIG. 6. The energy pulse can have any shape (e.g., as illustrated in FIG. 2(b)) and can even comprise a train of repeated individual energy pulses.

As shown in FIG. 6, a trigger time, t0, can be defined as the time an instruction is sent by an external emitter to the implanted controller to deliver a control energy pulse to the vagus nerve coupling unit (60). A delivery time, tv, is defined as the time the control energy pulse has actually been delivered to the vagus nerve. In case of a train of several pulses, the delivery time, tv; is the time the first pulse has been delivered. The delivery time, tv, cannot be measured directly with sufficient accuracy. By contrast, the trigger time, t0, is accurately defined and can be used for indirectly determining the value of the delivery time by estimating a trigger delay, $\delta t0$ The trigger delay, $\delta t0 = tv - t0$, between the trigger time and the actual time of delivery takes account of the time required for the instructions to arrive from an external control unit (150) to the internal control unit (54), via an external emitter (153e), for the time required by the implanted control unit (54) to process and forward the instructions to the energy pulse generator (51s), and for the time for the control energy pulse to reach the vagus nerve coupling unit (60). The determination of the delivery time, tv, is important for estimating a laryngeal signal time, tlx, at which a laryngeal electrical activity is expected. The laryngeal signal time, $tlx = tv + \Delta tp$, wherein $\Delta tp$ is the propagation time of a action potential to propagate along the vagus nerve from the vagus nerve coupling unit, to the laryngeal region, Lx, via a laryngeal nerve, Ln. The value of $\Delta tp$ in a healthy nerve can be estimated quite accurately.

The implanted controller (54) can also send via the implanted emitter (53e) a signal to the external receiver (153r) that the energy pulse generator (51s) has delivered an energy pulse. The time this signal is received by the external control unit (150) via the external receiver is defined as the delivery signal time, td. The delivery signal delay, $\delta td = td - tv$, between the trigger time and the actual time of delivery takes account of the processing time by the electronics and signal transfer time.

The exact value of the delivery time, tv, is very difficult to assess, since there is no direct access to the implanted AIMD. Similarly, the delays, $\delta t0$ and $\delta td$, depend mainly on the processing speed of the electronics and are difficult to assess, and can vary from one piece of equipment to another. The delays, $\delta t0$ and $\delta td$, are, however, of the order of the ms, such as about 1 to 10 ms, and can be estimated precisely. By crossing the trigger time, t0, and the delivery time, td, it is possible, (a) to ensure that a control energy pulse has been generated and (b) to estimate the actual value of the delivery time, tv, comprised between t0 and td.

In a preferred embodiment, the vagus nerve coupling unit (60) can comprise a pulse feedback unit (71) described more in details below and configured for transferring an electrical or optical signal through the implanted energy transfer unit (41) to a feedback sensor (171) enclosed in the encapsulation unit and coupled to the implanted controller (54). The electrical or optical signal is indicative that an energy pulse has reached the vagus nerve coupling unit (60). Thus informed, the implanted controller can emit a signal via the implanted emitter that an energy pulse has reached the vagus nerve coupling unit. The time this information is received by the external control unit (150) can be defined as the feedback time, tf, illustrated in FIG. 6. The feedback delay, $\delta tf = tf - tv$, is also dependent on the speed of electronic processing and of transfer of information and on the speed of propagation of the energy pulses through the implanted energy transfer unit (41). The feedback delay can be precisely determined with a proper calibration. The information related to the feedback time tf is very important as it ensures that an energy pulse has reached the vagus nerve coupling unit (60).

AIMD: Energy Pulse Generator (51S)

The energy pulse generator (51s) can generate electrical pulses or light pulses, preferably in a wavelength ranging between 350 and 1650 nm. Electric pulse generators are well known in the art, and the present invention is not restricted to any particular model, as long as it can generate electric pulses according to a set of parameters suitable for stimulation of the vagus nerve, as discussed supra. An electric pulse generated by the electric pulse generator (51s) can be transported to the vagus nerve coupling unit (60) through the implanted energy transfer unit (41) comprising one or more electrical conductors (41e), such as conductive wires. The conductive wires can transport electrical energy pulses to the vagus nerve coupling unit (60) either to feed electrodes (61) or a light source (5Ld) of an optrode (62). This technology is well established and has pros and cons well known to the persons skilled in the art. One well recognized drawback of electrical conductors (41e) is their incompatibility to exposure to magnetic fields, as encountered in security portals in airports and secured buildings, and in medical magnetic resonance imaging (MRI).

Light pulse generators have been introduced more recently as a solution to render AIMD's compatible with security portals and MRI. Instead of electric pulses, a light pulse generator generates light pulses. A light pulse generator comprises one or more sources of light emission, typically light emission diodes (LED) or vertical-cavity surface-emitting laser (VCSEL), and optionally micro-optics components (e.g., lenses). The transportation of the light energy thus generated can be transported to the vagus nerve coupling unit through the implanted energy transfer unit (41) comprising one or more optical fibres (41f). For sealing the interior of the housing (50h), the light pulse generator (51s) can be separated from the optical fibres (41f) by a window transparent to the wavelengths of the emitted light. An example of encapsulation unit suitable for the present invention is described in WO2018068807. The light pulses thus transported to the vagus nerve coupling unit (60) can be directed onto the vagus nerve, thus forming an optrode (62), or can be transformed into electric energy pulses by a photovoltaic cell coupled to electrodes (61).

The present invention can be implemented with both electric and light pulse generators.

AIMD: Vagus Nerve Coupling Unit (60)

Figure 3A:
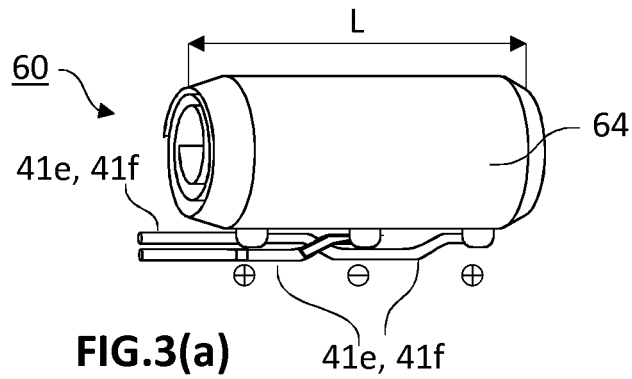
FIG. 3: shows various views of an embodiment of tripolar self-sizing cuff electrode suitable for the present invention.

As illustrated in FIG. 3, the vagus nerve coupling unit (60) comprises an insulating support (64) formed by an electrically non-conductive support sheet in the form of a tubular cuff structure of inner diameter, Dc, comprising an inner surface (64d) and an outer surface (64u). The vagus nerve coupling unit can also comprise at least a first electrode (61), generally two electrodes exposed at the inner surface of the cuff, separated from one another and forming a bipolar electrode as illustrated in FIG. 7(a)&(b). In a preferred embodiment the vagus nerve coupling unit comprises three electrodes exposed at the inner surface of the cuff, separated from one another, and forming a tripolar electrode, as illustrated in FIG. 3(a) wherein the presence of the electrodes is indicated by the signs (9, e). When the vagus nerve coupling unit (60) is coupled to a vagus nerve (Vn) the electrodes (61) contact a portion of the vagus nerve and form therewith an electrical stimulating circuit, as shown in FIGS. 3(a), 7(a), and 7(b).

Alternatively, or concomitantly, as illustrated in FIG. 7(c)&(d), the tubular cuff structure comprises at least a first optical contact (62), preferably two or more optical contacts exposed at the inner surface of the cuff.

The inner diameter, Dc, depends on the dimensions of the vagus nerve the cuff is to be wrapped around. The inner diameter, Dc, is preferably comprised between 3 and 5 mm±1 mm. The inner diameter, Dc, of the self-curling cuff and helical cuff electrode/optrode is generally comprised between 80 and 95% of the vagus nerve diameter. For split cylinder cuff electrodes/optrodes, the inner diameter, Dc, is generally equal to or slightly larger than the vagus nerve diameter. For example, Dc can be comprised between 100 and 110% of the vagus nerve diameter.

Insulating Support (64)

Figure 3B:
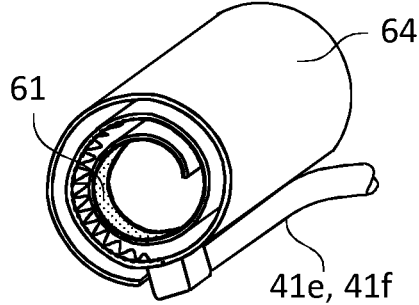
Figure 3C:
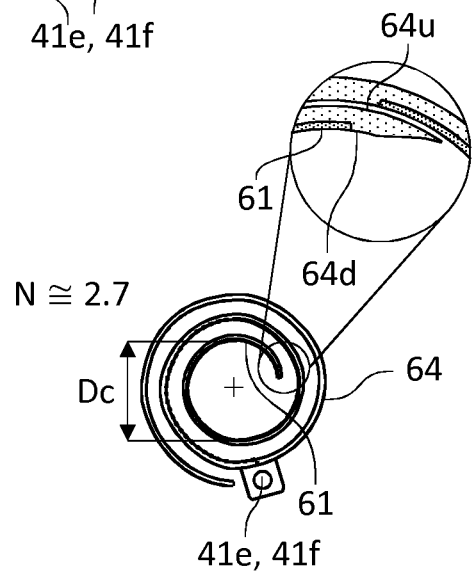

As mentioned supra, three main families of cuffs are available on the market:

Self-curling cuff (cf. FIG. 3(a)-(c)), wherein the electrically insulating support is made of a resilient material which is biased to spontaneously curl up around the vagus nerve. Self-curling cuff electrodes are particularly advantageous because their inner diameter of the lumen can vary depending on the diameter of the vagus nerve of a specific patient, or on variations of the diameter of the vagus nerve, following e.g., post-surgical inflammation or the like. Self-curling cuff electrodes are described e.g., in U.S. Pat. No. 4,602,624.

Split-cylinder cuff, wherein the electrically insulating support forms a cylinder with an open slit allowing insertion thereof over a cylindrical tissue. The slit is then closed. The cuff electrode is either provided with self-locking means or can be closed with external means, such as by ligaturing and the like. A flap may cover the slit. One drawback of slit cylinder cuff electrodes is that, once the slit is closed, the inner diameter thereof cannot vary anymore. Examples of slit cylinder cuff electrodes can be found e.g., in U.S. Pat. No. 8,155,757.

Helical cuff, wherein the electrically insulating support forms a helix wrapped around the vagus nerve. This geometry is very versatile, and several short helical cuffs can be positioned side by side at different distances, and their inner diameter can follow variations of the tissue diameter. Examples of helical cuff electrodes can be found e.g., in U.S. Pat. No. 5,964,702 or 8,478,428.

The insulating support (64) is made of a non-conductive material, preferably a polymer. If the insulating material must be deformed during implantation and for accommodating any body movement, for examples for self-curling cuff electrodes (cf. FIG. 3(a)-(c)) and, in some cases, for helical cuff electrodes, it is preferably made of an elastomeric polymer, such as silicone, a polyimide or polyurethane elastomer, or any biocompatible elastomer.

In self-curling cuffs, as shown in FIG. 3, the insulating support can be formed by a sheet material made of a single layer or can consist of a laminate comprising an inner sheet comprising the inner surface (64d) and an outer sheet comprising the outer surface (64u) either adhered directly to one another thus forming a two-layer laminate, or to one or more core layers, thus forming a multi-layered laminate with more than two layers. Self-curling cuff electrodes must be biased so that the insulating sheet material spontaneously rolls up to form a tubular cuff structure. This can be achieved with a laminate comprising at least two layers by pre-stretching the inner layer including the inner surface along an axis transverse to the axis of the tubular cuff, prior to and during adhesion thereof to an un-stretched outer layer including the outer surface. When a laminate is formed, the force pre-stretching the inner layer is released, and the inner layer contracts back to its equilibrium dimension along the transverse axis thus curling the sheet into a tubular cuff.

Because of the Poisson's ratio inherent to every material, which is the transverse to axial strain ratio of a material, by stretching the inner sheet along the transverse axis, the inner sheet contracts along the longitudinal axis, Z, to an extent depending on the level of transverse stretching and on the value of the Poisson ratio of the sheet material. Upon releasing the stress on the inner sheet to allow it to contract back to its equilibrium configuration along the transverse axis, the inner sheet also expands along the axis of the tubular cuff and may thus form trumpet shaped cuff edges. Trumpet shaped cuff edges are detrimental to a good contact between the vagus nerve (Vn) and the electrode contacts (61) and can be responsible for current losses which are detrimental to the efficacy of the cuff electrode. To prevent trumpet edges from forming as the insulating support curls up to form a tubular cuff, it suffices to pre-stretch the inner sheet along the axis of the tubular cuff, too, by an amount corresponding to the product of the material's Poisson's ratio and the pre-stretching level of the inner sheet along the transverse axis. If some level of trumpet shaped edges were desired, a fraction only of the foregoing pre-stretching along the axis of the tubular cuff could be applied instead.

It is preferred that the self-curling tubular cuff surrounds the vagus nerve with a number N of loops comprised between 1 and 3.5, preferably between 1.5 and 3.0, more preferably between 2.2 and 2.8. In FIG. 3(b)&(c), self-curling cuff electrodes curled with a number N≅2.7 of loops are illustrated. As illustrated in the inset of FIG. 3(c), the inner edge of the support sheet extending along the axis of the cylindrical cuff can be bevelled to smoothen the transition zone where a first loop ends, and a second loop starts thus eliminating the sudden step which would be formed with a straight edge and protecting the vagus nerve from injuries.

For helical cuffs, the number, N, of coils formed by each helical unit can be comprised between 1 and 5, preferably between 1.5 and 3, more preferably between 2 and 2.5. For split cylinder cuffs, the number N of loops can be comprised between 0.7 and 1.2, preferably between 0.8 and 1.0. For N<1, a flap is generally provided to cover the open slit remaining after implantation.

Electrodes (61)

The vagus nerve coupling unit (60) of the present invention further comprises at least a first electrode (61), generally at least a second electrode and, in a preferred embodiment, at least a third electrode, each electrode being exposed at the inner surface (64d) of the insulating support, such as to be in electrically conductive contact with the vagus nerve when the AIMD is implanted. The electrodes are also remote from the outer surface forming the exterior of the cuff. The at least one electrode is separated from the free edges of the insulating support to confine the current within the section of tissue comprised between the first and second electrodes, and to minimize current losses, straying beyond the boundaries of the cuff electrode.

As shown in FIG. 3(a), a cuff electrode according to the present invention may be tripolar, i.e., comprising three electrodes (in FIG. 3(a) the presence of the electrodes is indicated by the signs 9, e). A tripolar cuff electrode can be advantageous over a bipolar cuff electrode (i.e., comprising two electrodes), in that the current is confined within the cuff, thus reducing current losses in the surrounding tissues and fluids.

The electrodes (61) are made of a conductive material, which must be biocompatible and long-term stable in a physiological environment. Typically, gold, platinum, iridium, and alloys thereof can be used for the electrode contacts. The electrodes can be in the form of continuous stripes surrounding part or the whole of the circumference of the vagus nerve. Metal stripes can be glued or welded to the inner surface (64d) of the cuff or can be sandwiched between two layers of insulating material, the inner layer comprising the inner surface (64d) being provided with a window exposing the metal stripes at the inner surface. The electrodes can also be printed or otherwise deposited (e.g., by physical vapour deposition (PVD) or by chemical vapour deposition (CVD)) onto the inner surface (64d) of the insulating support.

Because straight metal stripes cannot be stretched, thus impairing the advantage of self-curling and helical cuff electrodes of adapting to size variations of the vagus nerve, it can be advantageous to use stripes forming a serpentine, as shown in FIG. 3(b), cf. electrodes (61) instead of straight stripes as shown in FIG. 7(a)&7(b).

Optrodes (62)

As illustrated in FIG. 7(c)&7(d), instead of, or additionally to electrodes (61), the insulating support sheet can be provided with one or more optical contacts (62). An optical contact as defined herein can be either a light emitter or a light sensor, or both. In some applications, stimulation of a tissue by light emission is believed to be mainly due to localized heating of the tissue. For such applications, it is preferred that the light directed by the optical contact be in the infrared range, preferably in the range of 750 to 3000 nm, more preferably of 1200 to 1800 nm. The cuff optrode of the present invention, however, can be used with light beams of any wavelength.

An optical contact can be the end of an optical fibre, which is either bevelled or coupled to a lens, mirror, or other micro-optic device for directing and focusing a light beam towards a precise area of the vagus nerve. The optical fibre can be coupled directly to the housing (50h) and to the energy pulse generator (51s) housed therein as shown in FIG. 7(d). Alternatively, as shown in FIG. 7(c), a light emitting device (5Ld) located on an outer surface of the cuff can be electrically powered by the energy pulse generator generating electric pulses and being located in the housing. The energy pulse generator can be electrically coupled to the light emitting device by electrical conductors (41e) (e.g., conductive wires). The light emitting device (5Ld) can be coupled to an optical fibre (41f) or to one or more lenses for guiding the light towards the vagus nerve. The light emitting device (5Ld) can be a LED, a VCSEL or other laser diode which is mounted on the insulating sheet such as to be in direct optical contact with the tissue around which the cuff is wrapped. If the insulating sheet is transparent to the light wavelength emitted by the optical contact, then the light can be transmitted through the thickness of insulating sheet separating the optical contact from the inner surface (64d) of the insulating sheet. If the insulating sheet is not transparent enough for an efficient transmission of the light energy, then a window can be provided at the inner surface of the insulating sheet to expose the optical contact.

Feedback Unit (71)

In a preferred embodiment illustrated in FIG. 7, the vagus nerve coupling unit (60) comprises a pulse feedback unit (71) activated by electrical current flowing between two electrodes (61) or by light emitted by an optrode (62) of the vagus nerve coupling unit (60). The implanted energy transfer unit (41) comprises an electrical conductor (41e) or an optical fibre (41f) for transferring electrical or optical energy from the pulse feedback unit (71) to a feedback sensor (171) enclosed in the encapsulation unit and coupled to the implanted controller (54). The implanted controller (54) is coupled to an implanted emitter (53e) for sending a feedback signal to an external receiver (153r) coupled to the external control unit informing that the pulse feedback unit has been activated. The external control unit (150) is configured for saving a delivery signal time, td, representative of the actual delivery time, tv, a control energy pulse was actually delivered to the vagus nerve. The detection signal time, td, is defined as the time of reception by the external receiver and by the external control unit of a feedback signal from the implanted emitter (53e). The delivery signal time, td, is illustrated in FIG. 6.

The vagus nerve coupling units (60) illustrated in FIGS. 7(a)& 7(b) comprise at least a first and second electrodes (61) forming a stimulating electric circuit with the vagus nerve they are coupled to. The pulse feedback unit (71) comprises a feedback electric circuit in parallel with the stimulating electric circuit, and in energy communication with the feedback sensor (171). FIG. 7(a) shows a light source (5Ld) such as a LED which emits a light when powered by electrical current running in the stimulating electric circuit. The light source (5Ld) is in optical contact via an optical fibre (41f) with feedback sensor (171) which is a light sensor. FIG. 7(b) shows the feedback electric circuit is electrically coupled to the feedback sensor (171) via electrical conductors (41e).

In another embodiment illustrated in FIG. 7(c)&7(d), the vagus nerve coupling unit (60) comprises at least an optrode (62) and the pulse feedback unit (71) comprises a light collector (71c) for receiving light energy transmitted or scattered through the vagus nerve. The light collector (71c) can be one or more lenses focusing the light thus received and is coupled to the feedback sensor (171) of the implanted controller. FIG. 7(c) illustrates the light collector in optical communication with the feedback sensor (171) which is a light sensor, via an optical fibre (41f) (represented by a dashed line). FIG. 7(d) shows an embodiment wherein the light collector (71c) is coupled to a photovoltaic cell (5pv) transforming light energy into electrical energy which is transported to the feedback sensor (171) via electrical conductors (41e), such as conductive wires.

The optical fibres (41f) and/or electrical conductors (41e) coupling the pulse feedback unit (71) to the feedback sensor (171) are preferably enclosed in a sheath together with any optical fibres (41f) and/or electrical conductors (41e) coupling the energy pulse generator (51s) to the vagus nerve coupling unit (60), thus forming the implanted energy transfer unit (41).

AIMD: Implanted Energy Transfer Unit (41)

The nature of the implanted energy transfer unit depends on the type of energy pulse generator (51s) used as well as whether the vagus nerve coupling unit (60) comprises an electrode, an optrode, or both.

FIG. 7(b)&7(c) illustrates an energy pulse generator (51s) generating electric pulses, which are transported to the vagus nerve coupling unit (60) by means of electrical conductors (41e). Any standard electrically electrical conductors known in the art can be used in the present invention depending on the applications. If the vagus nerve coupling unit (60) comprises electrodes (61) as illustrated in FIG. 7(b), the electrical conductors (41e) can be coupled directly to the electrodes to form an electric circuit with the vagus nerve. If, on the other hand, the vagus nerve coupling unit (60) comprises optrodes (62) as is the case in FIG. 7(c), the electrical conductors (41e) can be electrically coupled to a light emitting device (5Ld) to power it to generate light pulses directed onto a surface of the vagus nerve.

FIG. 7(a)&7(d) illustrates an energy pulse generator (51s) generating light pulses, which are transported to the vagus nerve coupling unit (60) by means of one or more optical fibres (41f). If the vagus nerve coupling unit (60) comprises optrodes (62) as illustrated in FIG. 7(d), the one or more optical fibres (41f) can be optically coupled directly to a surface of the vagus nerve. If, on the other hand, the vagus nerve coupling unit (60) comprises electrodes (61) as is the case in FIG. 7(a), the one or more optical fibres (41e) can be optically coupled to a photovoltaic cell (5pv) to transform the light pulse energy into electric pulse energy to feed the electrodes (61) and form therewith an electric circuit including the vagus nerve (Vn).

External Controller Device (ECD) (100)

The external controller device is the gist of the present invention, as it allows the non-invasive monitoring of the vagus nerve (Vn) activation. The external controller device comprises a laryngeal electrode unit (160), an external energy transfer unit (141), and an external control unit (150). The external controller unit is used exclusively for testing the functions of an implanted AIMD, and for determining an acceptable set of parameters of energy pulses.

ECD: Laryngeal Electrode Unit (160)

Figure 4A:
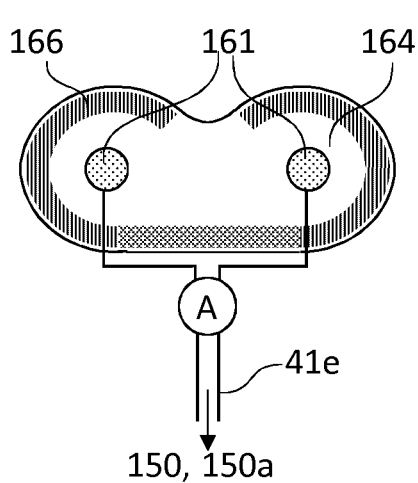
FIG. 4: shows two embodiments of laryngeal electrode unit according to the present invention (a) with an electrical feedback to the external control unit and (b) with an optical feedback.
Figure 4B:
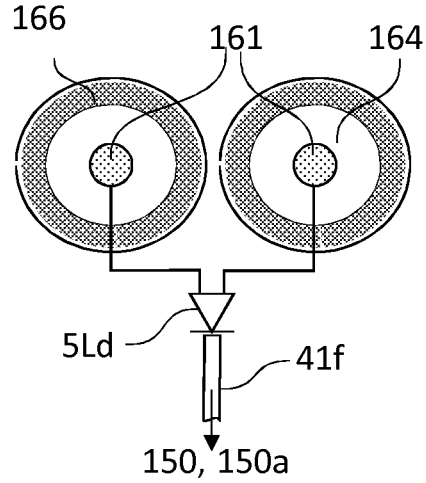

Embodiments of laryngeal electrode units (160) are illustrated in FIG. 4. A laryngeal electrode unit (160) can comprise a support sheet (164) which is electrically insulating and is preferably flexible to conform to the morphology of a laryngeal region (Lx) of a patient. The support sheet illustrated in FIG. 4(a) has a perimeter including a recess to wrap around a protruding larynx, and the one illustrated in FIG. 4(b) is divided into two separate patches. Any other geometry suitable for supporting electrodes in the laryngeal region can be applied instead. For example, many EEG and ECG electrodes as are commonly used for electrocardiograms and the like are suitable for use in a laryngeal electrode unit (160). The support sheet can be made of a fabric of woven, braided, or non-woven fibres, preferably polymeric fibres, or can be made of a flexible polymeric material, preferably an elastomer such as a silicone or polyurethane elastomer.

The support sheet (164) comprises an inner surface which supports two electrodes (161) (or more). As shown in FIG. 5, the laryngeal electrode units (160) is positioned at the laryngeal region (Lx) such that the two or more laryngeal electrodes (161) contact the skin of the patient over laryngeal nerves (Ln) or laryngeal muscles, preferably intrinsic muscles of the larynx, such as the cricothyroid muscle, the cricoarytenoid muscles (posterior or lateral), thyroarytenoid muscle or arytenoid muscles (oblique, or transverse). All the intrinsic muscles of the larynx (except the cricothyroid) are innervated by the inferior laryngeal nerve—the terminal branch of the recurrent laryngeal nerve, itself a branch of the vagus nerve (Vn). The cricothyroid is innervated by the external branch of the superior laryngeal nerve—again derived from the vagus nerve (Vn). The laryngeal electrodes (161) record any electric signal propagating through the laryngeal muscles.

As illustrated in FIG. 5, an external energy transfer unit (141) comprising one or more electrical conductors or optical fibres ensures the transfer of any electrical or optical signal representative of the electrical laryngeal activity recorded by the laryngeal electrodes to an external control unit (150) or to an intermediate controller (150a) in communication with the external control unit (150). The communication between the intermediate controller (150a) and the external control unit can be carried through wiring (electrical conductors or optical fibres) or preferably by wireless transmission means, such as RF, Bluetooth, and the like. As shown in FIG. 4(a) an amplifier (A) may be used to enhance the strength of the signal. Filters can also be applied. FIG. 3(b) shows an embodiment wherein the external energy transfer unit (141) comprises an optical fibre. The laryngeal electrodes can be coupled to a LED in optical contact with the optical fibre to transfer an optical signal. Here again, an amplifier (A) (not shown) can be used to strengthen the optical signal.

To stabilize the laryngeal electrodes (161) at the laryngeal region (Lx) and to ensure an optimal contact with the laryngeal region, the inner surface of the support sheet (164) may be provided with an adhesive layer (166), extending along at least a portion of the perimeter of the support sheet, or extending over part or all of the area of the inner surface. The adhesive can be a pressure sensitive adhesive (PSA) or any adhesive used in medical adhesive tapes or plasters.

ECD: External Control Unit (150)

The external control unit comprises,
  a setting unit (151) for entering control pulse parameters of a control energy pulse,
  an external emitter (153e) configured for sending a signal to the implanted receiver (53r), and
  a converter converting electrical or optical signals transferred by the external energy transfer unit (141) into a visual (155) or acoustic (157) display The external control unit (150) can also comprise an external receiver (153r) for receiving signals from an implanted emitter (53e).

Figure 5A:
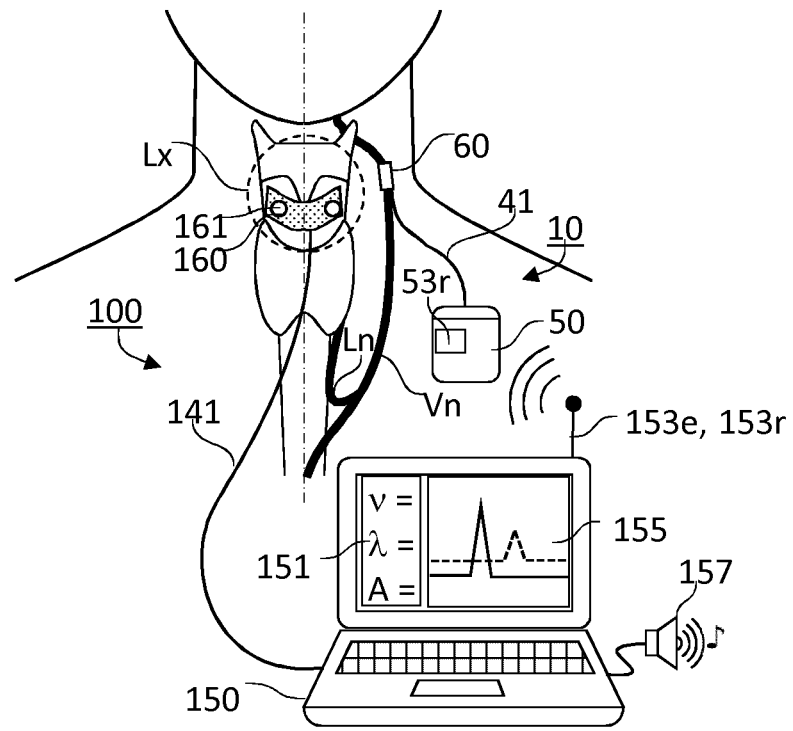
FIG. 5: shows an implanted AIMD with the vagus nerve coupling unit coupled to the vagus nerve, and three embodiments of external controller devices according to the present invention.
Figure 5B:
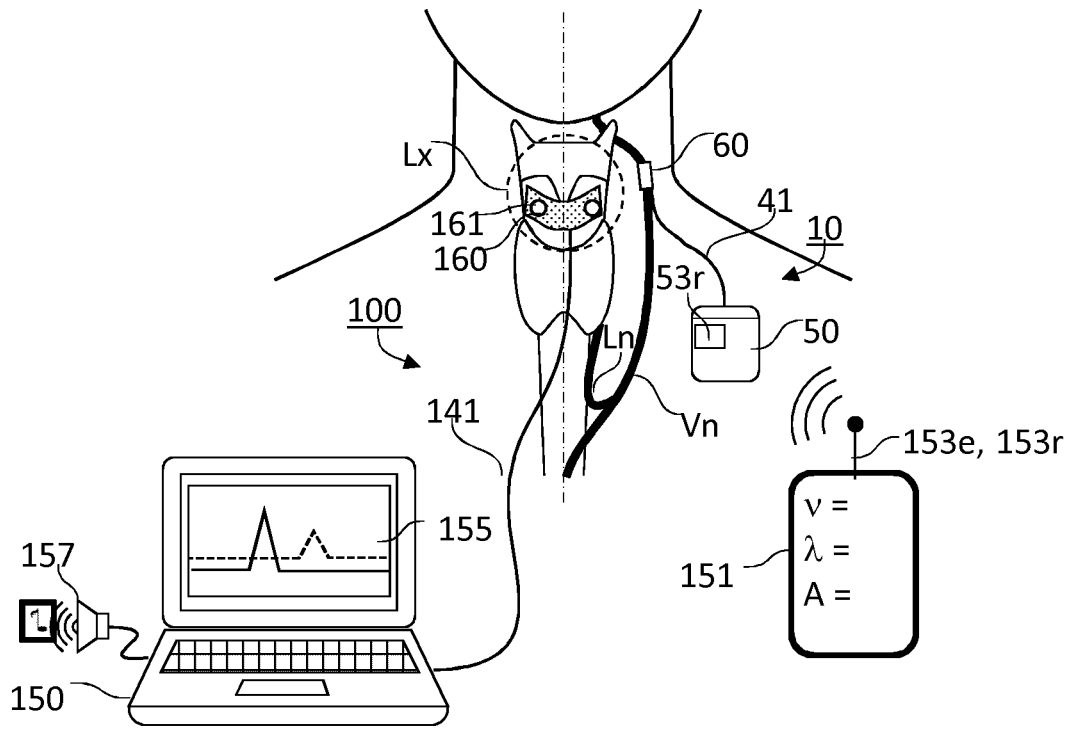
Figure 5C:
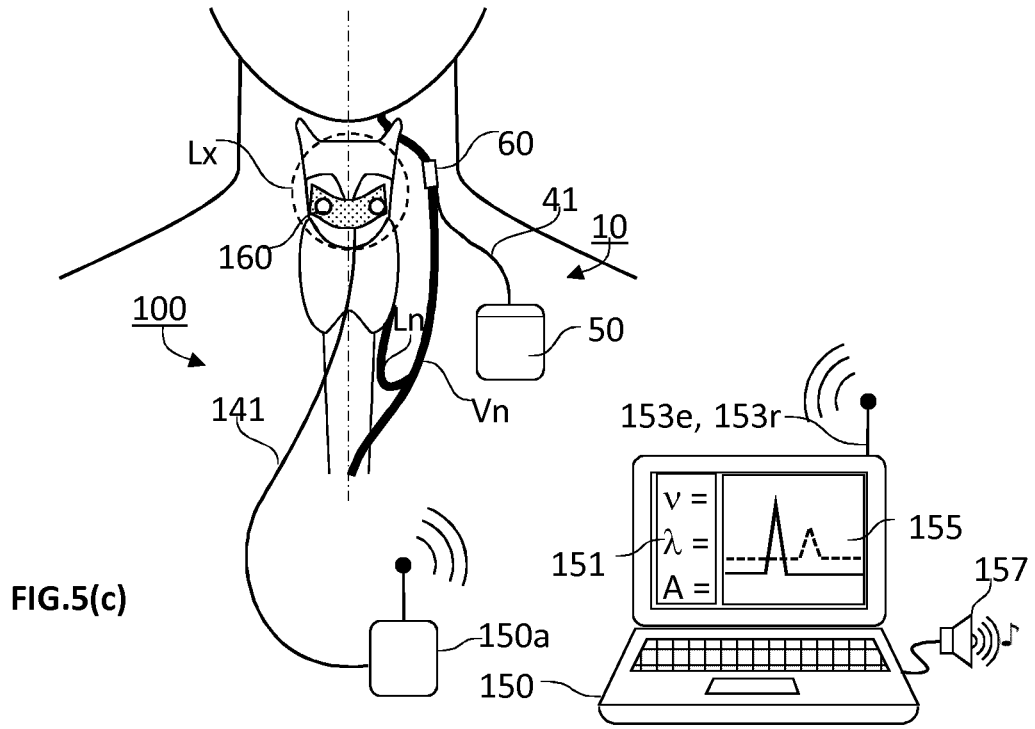

The setting unit (151) can be integrated in a personal computer or laptop, and the like, as illustrated in FIG. 5(a)&5(c) or in a tablet or smart phone as illustrated in FIG. 5(b). The setting unit is configured for entering and storing a set of control pulse parameters, including one or more of intensity (I1, I2), duration (d1, d2), number (N), frequency (f1, f2) of deliveries, shape of the pulses, etc., as defined in FIG. 2(b). A set of control pulse parameters differs from a therapeutic set of pulse parameters in that its goal is not therapeutic but merely of control. In particular, a set of control pulse parameters is used to assess whether the implanted AIMD functions, and that it is properly coupled to the vagus nerve so as to deliver energy pulses thereto. It can also be used to determine the activation threshold intensity below which a detectable compound action potential is not propagated along the vagus nerve. For example, when a therapeutic set of pulse parameters may include successive trains of N pulses of a given duration (d1, d2), and of given shape, a set of control pulse parameters would generally comprise a single pulse, or a single train of n pulses (n<N).

When a therapeutic set of pulse parameters must have a therapeutic effect on a patient and must follow a predefined therapeutic plan, a set of control parameters needs not follow any therapeutic plan and does not have any therapeutic effect. It suffices that the set of control parameters activates a vagus nerve in a way that an action potential propagates along the vagus nerve and along a laryngeal nerve. If all the control parameters are above corresponding threshold values, an electrical signal can be measured at the laryngeal area, Lx, representative of the functioning of the AIMD.

The external emitter (153e) is coupled to the setting unit (151) and is configured for sending a signal to the implanted receiver (53r) instructing the implanted controller (54) to trigger the delivery by the energy pulse generator (51s) to the vagus nerve coupling unit (60) of one or more control energy pulses defined by the control pulse parameters entered in the setting unit (151). The signal sent by the external emitter is an electromagnetic signal, preferably an RF signal or an optical signal in the wavelengths range of 350 to 1600 nm. For optical signals between the external emitter (153e) and implanted receiver (53r), it is preferred that the implanted receiver (53r) be located as close as possible to the skin of the patient, preferably separated from an outer surface of the patient's skin of not more than 20 mm, preferably not more than 10 mm, more preferably not more than 5 mm.

The converter is configured for converting electrical or optical signals transferred by the external energy transfer unit (141) from the laryngeal coupling unit (60) to the external control unit (150) (either directly or via an intermediate controller (150a)) into a visual (155) or acoustic (157) display indicative of the intensity of the laryngeal electrical activity (cf. FIG. 5). An example of visual display of such signal is illustrated in FIG. 6, showing two examples of control pulses (V1, V2) (=solid line) and the corresponding electrical signals (L1, L2) (=dashed lines) detected by the laryngeal electrodes (161). The control pulse (V1) yielded no detectable laryngeal peak (L1) corresponding to the propagation of the control pulse (V1). By contrast, the control pulse (V2) yields a clear peak (L2) on the laryngeal electrical signal. The magnitude of the peak thus displayed is proportional to the magnitude of the electric signal recorded by the laryngeal electrodes.

In a preferred embodiment, the implanted controller comprises an implanted emitter (53e) for sending a signal to the external control unit (150) informing that a control energy pulse has been delivered by the energy pulse generator (51s). The external controller can save a corresponding delivery signal time, td. The implanted emitter can also send a signal to the external control unit (50) informing that a control energy pulse has reached the vagus nerve coupling unit (60), as assessed by the pulse feedback unit (71) described supra. The external control unit comprises an external receiver (153r) for receiving signals sent by the implanted emitter (53e), The external control unit can be configured for saving a trigger time, t0, delivery signal time, td, and a feedback time, tf. The trigger time, t0, and the delivery signal time, td, are both representative of the time, tv, a control energy pulse was delivered to the vagus nerve. As illustrated in FIG. 6, the trigger time t0 is the time a signal was sent by the external emitter (153e) to the implanted receiver (53r) instructing to deliver one or more control energy pulses, and the delivery signal time, td, is the time a signal was received by the external receiver (53r) from the implanted emitter (53e) informing that an energy pulse had been delivered by the energy pulse generator (51s).

The feedback time, tf, is the time a signal was received by the external receiver (153r) from the implanted emitter (53e) informing that an energy pulse had reached the vagus nerve coupling unit (60). This information was generated via the pulse feedback unit (71) and feedback sensor (171) discussed supra with respect to FIG. 7.

The knowledge of the trigger time, t0, allows the determination within a high accuracy (by the determination of the trigger delay, δt0) of the delivery time, tv, an energy pulse was delivered to the vagus nerve coupling unit (60) (cf. FIG. 6). The trigger time delay, δt0, depends on the communication speed between the setting unit (151) and the implanted controller (54), as well as processing time of the implanted controller (54) to instruct the energy pulse generator to deliver an energy pulse and the propagation speed along the implanted energy transfer unit (41).

The knowledge of the delivery signal time, td, (a) confirms that a control energy pulse (V1, V2) has been delivered by the energy pulse generator (51s) and (b) increases the accuracy of the determination of the delivery time, tv, by the determination of the delivery signal time delay, δtd. The delivery signal time delay, δtd, depends on energy transfer speed between the pulse feedback unit (71) and the feedback sensor (171), as well as the communication time between the implanted controller (54) and the external controller (150). In general, both t0 and 8td are of the order of the milliseconds.

Electrocardiogram

The cardiac activity is inevitably recorded by the laryngeal electrodes (161). The signal of an electrocardiogram can mask a signal of laryngeal activity. For this reason, the kit of parts can further comprise a device for measuring an electrocardiogram of the patient coupled to the external control unit (150). The device can be a separate device for measuring an electrocardiogram or it is preferably formed by the laryngeal electrodes (161). Alternatively, the device can be lodged in the encapsulation unit in connection with the vagus nerve coupling unit (60). The device is connected to the external control unit which can then be configured for synchronizing the trigger time, t0, for sending a signal to deliver to the vagus nerve coupling unit (60) one or more control energy pulses such that the laryngeal signal time, tlx, at which a laryngeal electrical activity (L1, L2) is detected corresponds to an isoelectric period of the electrocardiogram. Isoelectric periods in an electrocardiogram are of the order of the second, whilst the time delay, Δt, between the trigger time, t0, and the time, tlx, of detection of a laryngeal signal is of the order of the milliseconds or at most of the centiseconds. The synchronization of the trigger time, t0, or laryngeal signal time, tlx, is easy to achieve. The isoelectric period is defined as both period ST between the end of an S wave and the beginning of a T wave, and period TP between the end of a T wave and the beginning of a P wave, that is, when no potential is recorded because the electrical forces are acting in different directions and neutralize each other.

Method for Adjusting the Parameters of an AIMD Coupled to a Vagus Nerve

The present invention also concerns a method for adjusting the parameters of an implanted stimulating device coupled to a vagus nerve of a patient. The method comprises the following steps illustrated in a flowchart in FIG. 8.

(a) Providing a patient having an implantable stimulating device (10) as defined supra implanted in its body, with the vagus nerve coupling unit (60) coupled to a vagus nerve (Vn) of the patient, (b) Providing an external controller device (100) as defined supra, and coupling the laryngeal electrode unit (160) to a skin of the patient in the laryngeal region (Lx), (c) Entering a set of parameters defining a control energy pulse (V1, V2) into the setting unit (151), (d) sending through the external emitter (153e) a signal to the implanted receiver (53r) instructing the energy pulse generator (51s) to deliver to the vagus nerve coupling unit (60) one or more control energy pulses (V1, V2) as defined by the set of parameters, (e) defining a trigger time, t0, representative of a delivery time, tv, at which a control energy pulse was delivered to the vagus nerve, wherein t0 is defined as the time the signal was sent by the external emitter (153e) to the implanted receiver (53r) to deliver one or more control energy pulses, (f) controlling whether the laryngeal electrode unit (141) records a laryngeal electrical activity (L1, L2) delayed from the trigger time, t0, by a predefined control time range, $\Delta t \pm \delta t$, with $\delta t < \Delta t$.

The delay $\Delta t$ between the trigger time, t0, and the laryngeal signal time, tlx, is due, on the one hand, to AIMD related issues, including speed of information transfer between emitters and receivers, processing speed of the controllers, and energy pulse transfer speed along the implanted energy transfer unit and, on the other hand, on physiological reasons, including the propagation speed of a compound action potential along the vagus nerve and a branched laryngeal nerve. This physiological delay (sometimes referred to as latency time) is referred to as $\Delta tp$ in FIG. 6.

The physiological delay, $\Delta tp$, is an important measurement value with important clinical significance. A given physiological delay value is indeed expected from a healthy nerve depending on the lengths of nerves separating the vagus nerve coupling unit (60) from the laryngeal region, Lx. Physiological delays longer than the expected value can be indicative that a nerve is not in a healthy state and that it is more or less demyelinated. Physiological delays shorter than the expected value may be indicative that a laryngeal electrical signal may not originate from the delivery of a control energy pulse.

This method allows the assessment of whether,
the implanted AIMD works properly and has been implanted correctly so that
an energy pulse (V1, V2) of a satisfactory set of control parameters has been delivered by the energy pulse generator (51s) to the vagus nerve coupling unit (60),
the energy pulse has generated a compound activation potential which has propagated along the vagus nerve and laryngeal nerves to the laryngeal region, Lx.

Figure 8:
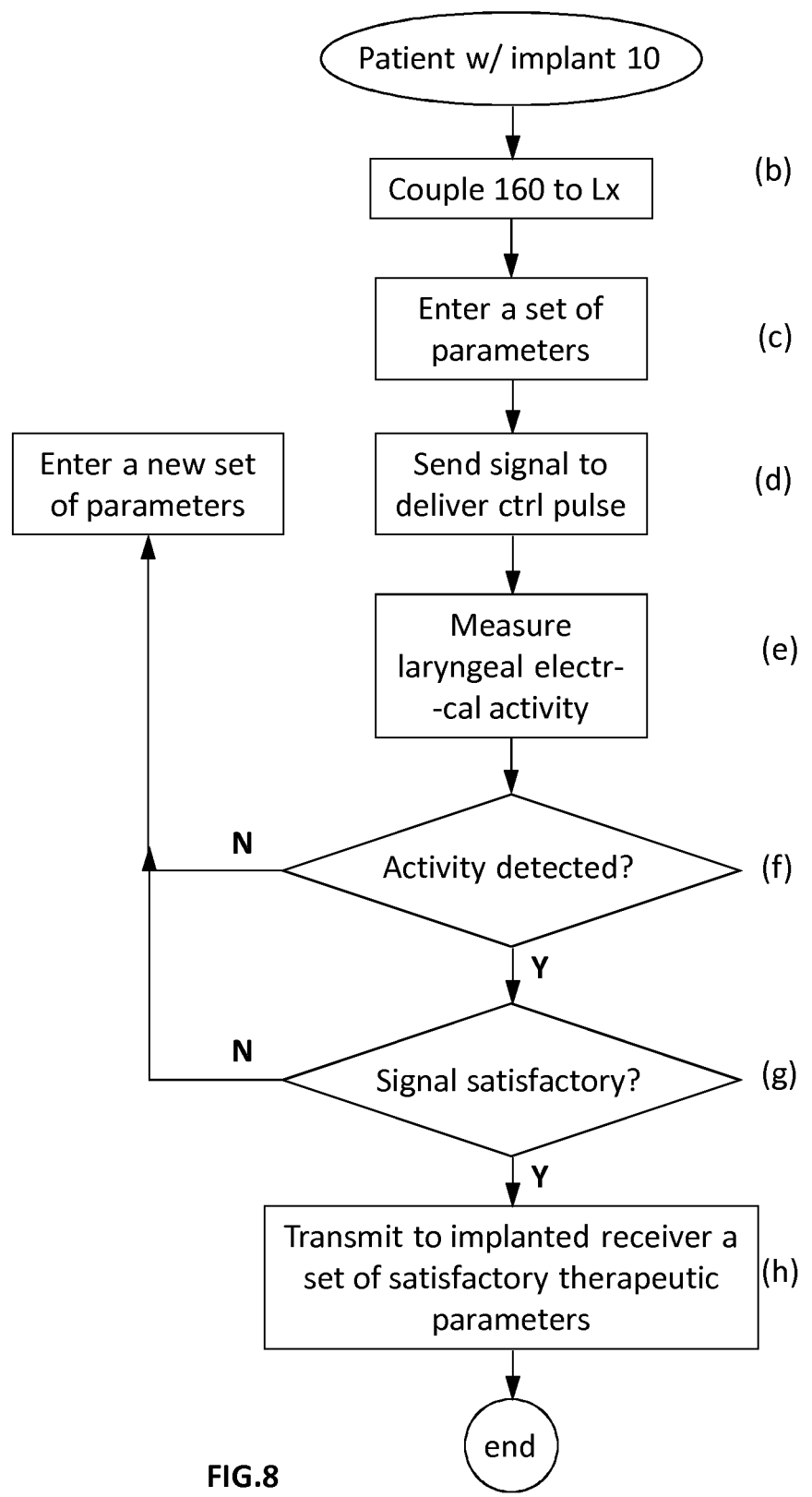
FIG. 8: shows a flowchart indicating the steps for determining a satisfactory set of control parameters defining therapeutic energy pulses to be delivered to the vagus nerve of a patient according to a therapeutic plan.

As shown in FIG. 8 at step (f)→N, if no laryngeal electrical activity (1) attributed to the energy pulse (V1) is recorded within the propagation time range, $\Delta t \pm \delta t$, the method comprises the further step of entering into the setting unit (151) a second set of parameters defining a second control energy pulse (V2), and repeating steps (d) to (f, with the second set of parameters. FIG. 6 illustrates two displays of the laryngeal electrical activity L1, L2, resulting from the delivery of an energy pulse V1, V2, characterized by two sets of control parameters differing from one another by two different values of the intensity of the energy pulses. The energy pulse V1 has an intensity such that no laryngeal electrical activity L1 attributed to the energy pulse V1 can be recorded within the propagation time range, $\Delta t \pm \delta t$. This can be due to several reasons. For example, a first reason can be that the energy pulse V1 is intrinsically has an intensity value below the intensity threshold value. Second, the contact between the vagus nerve coupling unit and the vagus nerve may not be optimal, thus increasing the value of the intensity activation threshold. Third, the vagus nerve of a patient may be damaged. Fourth, no energy pulse has been delivered by the energy pulse generator (51s) or no energy pulse has reached the vagus nerve coupling unit (60).

As illustrated in FIG. 8 at (f)→Y, and (g), when a laryngeal electrical activity (L1, L2) is recorded within the propagation time range, $\Delta t \pm \delta t$, the method comprises the further step of comparing said laryngeal electrical activity with a predefined criterion of satisfaction.

As shown in FIG. 8 at (g)→N, if the laryngeal electrical activity (L1, L2) thus recorded does not fulfil the predefined criterion, then the method comprises the step of entering into the setting unit (151) a new set of parameters defining a new control energy pulse, and repeating steps (d) to (f), with the new set of parameters. These operations are repeated until a laryngeal electrical activity (L1, L2) is detected that fulfils the predefined criterion.

As shown in FIG. 8 at (g)→Y, and (h), when the laryngeal electrical activity (L1, L2) thus recorded fulfils the predefined criterion, then the method comprises the step of transmitting the corresponding set of parameters of the control energy pulse to the implanted controller (54) for saving it as a satisfactory set of control parameters from which a therapeutic set of parameters can be defined to match a therapeutic plan.

The set of parameters may include one or more of a pulse frequency, a pulse amplitude, a pulse duration, a pulse interval, a pulse number. A given set of parameters entered at step (c) can be saved in a memory to form a set of saved parameters. At step (d), the energy pulse generator (51s) can be instructed to deliver sequentially several times to the vagus nerve coupling unit (60) control energy pulses (V1, V2) as defined by the set of saved parameters.

By sequentially instructing N times the energy pulse generator (51s) to deliver to the vagus nerve coupling unit one or more control energy pulses (V1, V2) as defined by a given set of parameters, and by recording the laryngeal electrical activity (L1, L2) by the laryngeal electrode unit (160), the laryngeal electrical signal (L1, L2) can be averaged over the N repetitions of step (f), wherein N is a natural number greater than 1. This way, the signal to noise ratio can be enhanced substantially.

As discussed supra, and to prevent the heart activity to interfere with the laryngeal electrical signal (L1, L2), an electrocardiogram of the patient can be measured and communicated to the external control unit (150) or to the implanted controller (54). The external control unit (150) or the implanted controller (54) can then synchronize the delivery to the vagus nerve coupling unit (60) of one or more control energy pulses to correspond to an isoelectric period of a cardiac cycle of the patient. If the synchronization is controlled by the external control unit (150), then the trigger time, t0, is set accordingly. In other words, the external control unit (150) can decide to delay the emission of the instruction to the implanted controller (54) with respect to the moment an operator sent the instruction, until the signal delivery can be synchronized with the electrocardiogram of the patient. If, on the other hand, the synchronization is controlled by the implanted controller (54), then the trigger time, t0, is clearly set and the implanted controller (54) is instructed as soon as the operator sent the instruction, but the implanted controller (54) can decide to delay the delivery of an energy pulse to ensure that the corresponding laryngeal electrical signal does not interfere with the electrocardiogram.

Synchronizing the delivery of an energy pulse relative to the electrocardiogram of a patient generates a variation of the trigger time delay, $\delta t0$ (cf. FIG. 6). In these conditions, a pulse feedback unit (71) suitable for informing the external control unit (150) of the delivery signal time, td, is advantageous to better define the delivery time, tv, and thence the period tlx±δ within which a laryngeal electrical signal (L1, L2) is expected.

SUMMARY AND ADVANTAGES

The present invention provides a simple and reliable solution to a number of distinct issues related to the therapeutic treatment of various diseases by the stimulation of the vagus nerve. For such therapeutic treatment to be successful, a number of conditions must be fulfilled in combination. One missing link and the whole chain is disrupted. It is difficult to identify the cause of a malfunction as the AIMD is implanted in a body and not accessible. A stimulated nerve may not be activated for a number of causes.

The energy pulse generator (51s) may have a defect, the battery can be low, or the transfer of an energy pulse to the vagus nerve coupling unit (60) can be disrupted.

Next, the AIMD may function perfectly, but the vagus nerve coupling unit (60) may not be optimally coupled to the vagus nerve (Vn) to transfer the energy pulse to the vagus nerve. The tubular cuff can for example be too loose or folded in reverse.

The value of one or more control parameters characterizing a control stimulation pulse may be below the activation threshold of said parameter. The activating threshold may indeed vary from one patient to another and with time in a same patient. The variation of activation threshold from one patient to another is increased by the fact that the vagus nerve coupling unit can be implanted more or less loosely as discussed supra, which must be added to the physiological activation threshold of the vagus nerve. A therapeutic treatment carried out below the activation intensity can therefore render the whole therapy useless.

Finally, the vagus nerve can be damaged to a point that it is not reactive to energy pulses of intensities within a safety range (i.e., the activation threshold is higher than the safety range). This situation is totally independent of the AIMD, but renders the whole therapy useless, nonetheless.

The present invention allows the periodic assessment of the good functioning of the implanted AIMD and of the nerve health. If a malfunction such as described above appears, the present invention allows discriminating the source of the malfunction. The present invention also allows the determination of a therapeutic set of parameters suitable for the implementation of a therapeutic plan.

The present invention permits to assess whether an implanted AIMD is in working conditions. Upon receiving the instruction from the external control unit (150) the implanted controller (54) can inform the external controller that an energy pulse has been delivered by the energy pulse generator (51s). This permits to determine whether there is any problem within the encapsulation unit (50).

The pulse feedback unit (71) can inform that an energy pulse, delivered from the energy pulse generator (51s) lodged in the housing (50h) of the encapsulation unit, has reached the vagus nerve coupling unit (60). This permits to determine whether there is any problem within the implanted energy transfer unit (41) and/or the vagus nerve coupling unit (60).

The detection of a laryngeal electrical signal (L1, L2) corresponding to the delivery of an energy pulse (V1, V2) informs the operator that the coupling of the vagus nerve coupling unit to the vagus nerve is satisfactory and that the vagus nerve is reactive to energy pulses.

One great advantage of the present invention also includes the fact that an operator controls the delivery time, tv, of a control pulse, and knows when a laryngeal signal (L1, L2) is expected in a range tlx±δ. If a laryngeal signal is detected substantially out of that range, it can be concluded that it is representative of a problem or that it has another origin than the delivery of a control pulse. By contrast, many prior art devices rely on the delivery of a therapeutic pulse according to a therapeutic set of parameters programmed in the implanted controller, and over which the operator has no direct control. The operator therefore does not have an exact knowledge of the delivery time, tv, let alone of the laryngeal signal time tlx±δ.

Finally, by comparing the recorded laryngeal electrical activity (L1, L2) with a predefined criterion of satisfaction, it is possible to define a satisfactory set of control parameters, which can be used to define a therapeutic set of parameters for the implementation of a therapeutic plan established by a practitioner.

The laryngeal electrode unit (160) is very small and light, and the coupling to the laryngeal region (Lx) is easy and quite comfortable for the patient. The signal received is reliable and quantitative, allowing the determination of a therapeutic set of parameters.

| Ref# | Feature |
| --- | --- |
| 5Ld | Light source (LED) |
| 5pv | Photovoltaic cell |
| 10 | AIMD |
| 41 | Implanted energy transfer unit |
| 41e | Electrical conductor |
| 41f | Optical fibre |
| 50 | Encapsulation unit |
| 50h | Housing |
| 51s | Energy pulse generator |
| 52 | Source of power |
| 53e | Implanted emitter |
| 53r | Implanted receiver |
| 54 | Implanted controller |
| 60 | Vagus nerve coupling unit |
| 61 | electrode |
| 62 | optrode |
| 64 | Insulating support |
| 64d | Inner surface |
| 64u | Outer surface |
| 71 | Pulse feedback unit |
| 71c | Light collector |
| 100 | External controller device |
| 141 | external energy transfer unit |
| 150 | External control unit |
| 150a | Intermediate controller |
| 151 | Setting unit |
| 153e | External emitter |
| 153r | External receiver |
| 155 | Visual display |
| 157 | Acoustic display |
| 160 | Laryngeal electrode unit |
| 161 | Laryngeal electrode |
| 164 | Support sheet |
| 166 | Adhesive |
| 171 | Feedback sensor |
| A | Amplifier |
| d1, d2 | Duration of an energy an energy pulse |
| Dc | Inner diameter of tubular cuff |
| f1, f2 | Energy pulse frequency |
| I1, I2 | Energy pulse intensity |
| L | Cuff length along the tubular axis |
| L1, L2 | Laryngeal electrical signal |
| Ln | Laryngeal nerve |
| Lx | Laryngeal region |
| N | Number of folds of a tubular cuff |

-continued

| Ref# | Feature |
|---|---|
| R | Recovery pulse |
| S | Stimulating pulse |
| t0 | Trigger time |
| td | Delivery signal time |
| tf | Feedback signal time |
| tlx | Laryngeal signal time |
| tv | Delivery time |
| V1, V2 | Energy pulse |
| Vn | Vagus nerve |
| δ | Half range of expected period of recording of a laryngeal electrical signal |
| δt0 | Trigger time delay, tv − t0 |
| δtd | Delivery time delay, td − tv |
| δtf | Feedback time delay, tf − tv |
| Δt | Delay between trigger time and laryngeal signal time, tlx − t0 |
| Δtp | Physiological delay, tlx − tv |

The invention claimed is:

1. A kit of parts for the control of a delivery of an electric or electromagnetic pulse to a patient's vagus nerve by an implanted stimulating device, said kit of parts comprising:
(a) an implantable stimulating device comprising:
a vagus nerve coupling unit comprising one or more electrodes and/or an optrode mounted on an insulating support forming a cuff configured for being coupled directly to the patient's vagus nerve (Vn),
an encapsulation unit configured for being subcutaneously implanted at a location separated from the vagus nerve coupling unit, and comprising a housing enclosing,
an energy pulse generator, for delivering energy pulses including electrical or optical energy,
a source of power for activating the energy pulse generator,
an implanted controller configured for instructing the energy pulse generator to deliver energy pulses to the vagus nerve coupling unit, and
an implanted receiver for receiving signals from an external emitter,
an implanted energy transfer unit comprising one or more electrical conductors and/or optical fibres for transferring electrical and/or optical energy between the energy pulse generator of the encapsulation unit and the vagus nerve coupling unit;
(b) an external controller device comprising:
a laryngeal electrode unit comprising laryngeal electrodes configured for being coupled to the patient's skin on their neck at a level that corresponds to the patient's laryngeal region (Lx) for measurement of laryngeal electrical activity at the patient's laryngeal region, and
an external energy transfer unit comprising one or more electrical conductors or optical fibres for transferring an electrical or optical signal from the laryngeal electrode unit to an external control unit or to an intermediate controller in communication with the external control unit, the electrical or optical signal being representative of the laryngeal electrical activity measured at the laryngeal region: wherein
the external control unit comprises:
a setting unit for entering control pulse parameters of a control energy pulse;
an external emitter configured for sending a signal to the implanted receiver instructing the implanted controller to instruct the energy pulse generator to deliver to the vagus nerve coupling unit one or more control energy pulses defined by the control pulse parameters entered in the setting unit; and
a converter converting electrical or optical signals transferred by the external energy transfer unit into a visual or acoustic display indicative of the intensity of the laryngeal electrical activity measured at the laryngeal region; and
wherein the external control unit is configured for saving a trigger time, t0, defined as a time the signal was sent by the external emitter to the implanted receiver to deliver the one or more control energy pulses and using t0 to estimate within a narrow time window, ±δt, a time, tlx, when an electrical activity caused by the delivery of a control energy pulse of the one or more control energy pulses is detectable at the laryngeal region.

2. The kit of parts according to claim 1, wherein
the implanted controller comprises an implanted emitter for sending a signal to the external control unit informing that a control energy pulse has been delivered by the energy pulse generator; and
the external control unit comprises an external receiver for receiving signals sent by the implanted emitter, and for saving a delivery signal time, td, of a control energy pulse delivered to the vagus nerve, wherein td sets a time the external receiver received the signal sent by the implanted emitter informing that a control energy pulse has been delivered by the energy pulse generator.

3. The kit of parts according to claim 1, wherein
the vagus nerve coupling unit comprises a pulse feedback unit activated by electrical current flowing between two electrodes or by light emitted by the optrode of the vagus nerve coupling unit;
the implanted energy transfer unit is adapted to transfer the electrical and/or optical energy from the pulse feedback unit to a feedback sensor enclosed in the encapsulation unit and coupled to the implanted controller;
the implanted controller is coupled to an implanted emitter for sending a signal to the external control unit informing that the pulse feedback unit has been activated; and
the external control unit comprises an external receiver for receiving the signal sent by the implanted emitter, and is configured for saving a feedback signal time, tf, allowing an actual delivery time, tv, to be assessed, wherein v is a time the control energy pulse of the one or more control energy pulses was actually delivered to the vagus nerve.

4. The kit of parts according to claim 3, wherein the pulse feedback unit comprises a light collector for receiving light energy transmitted or scattered through tissue of the patient, said light collector being connected to the implanted controller either by an electrical conductor coupled to a photovoltaic cell, or directly by an optical fibre.

5. The kit of parts according to claim 3, wherein the pulse feedback unit comprises a feedback electrical circuit connected to the feedback sensor either by an electrical conductor or by an optical fibre coupled to a light emitting diode (LED).

6. The kit of parts according to claim 1, wherein the vagus nerve coupling unit is configured where the one or more electrodes are arraigned as a tripolar electrode with three electrodes separated from one another and exposed to an inner surface of the insulating support.

7. The kit of parts according to claim 1, further comprising:

a device for measuring an electrocardiogram of the patient coupled to the external control unit; and wherein the external control unit is configured for synchronizing the sending at the trigger time, t0, of the signal to deliver to the vagus nerve coupling unit the one or more control energy pulses such that the time, tlx, at which the electrical activity is detected and estimated from the trigger time, t0, corresponds to an isoelectric period of the electrocardiogram.

8. A method for recording laryngeal electrical activity (L1, L2), the method comprising:
(a) providing the kit of parts of claim 1;
(b) providing a patient having the implantable stimulating device implanted in the patient's body, with the vagus nerve coupling unit coupled to the patient's vagus nerve (Vn);
(c) providing the external controller device, and coupling the laryngeal electrode unit to the patient's skin in the laryngeal region (Lx);
(d) entering a set of control parameters defining a control energy pulse (V1) into the setting unit;
(e) sending through the external emitter a signal to the implanted receiver instructing the energy pulse generator to deliver to the vagus nerve coupling unit one or more control energy pulses (V1) as defined by the set of control parameters;
(f) defining a trigger time, t0, defined as the time the signal was sent by the external emitter to the implanted receiver to deliver one or more control energy pulses, and using t0 to estimate within a narrow time window, ±δt, the time, tlx, when an electrical activity caused by the delivery of the one or more control pulses is detectable at the laryngeal region; and
(g) controlling whether the laryngeal electrode unit records the laryngeal electrical activity (L1, L2) delayed from the trigger time by a predefined control time range, Δt±δt, with Δt<δt.

9. The method according to claim 8, wherein, if no laryngeal electrical activity (L1) attributed to the control energy pulse (V1) is recorded within the predefined control time range, Δt±δt, entering into the setting unit a second set of control parameters defining a second control energy pulse (V2), and repeating steps (e) to (g), with the second set of control parameters.

10. The method according to claim 8, wherein when the laryngeal electrical activity (L1, L2) is recorded within the predefined control time range, Δt±δt, comparing said laryngeal electrical activity with a predefined criterion of satisfaction, and
if the laryngeal electrical activity (L1, L2) thus recorded does not fulfil the predefined criterion, then entering into the setting unit a new set of control parameters defining a new control energy pulse, and repeating steps (e) to (g), with the new set of control parameters, and
if the laryngeal electrical activity (L1, L2) thus recorded fulfils the predefined criterion, then transmitting the corresponding set of control parameters of the control energy pulse to the implanted controller for saving it as a satisfactory set of control parameters of an energy pulse and defining a therapeutic set of parameters on the basis of the satisfactory set of control parameters.

11. The method according to claim 8, wherein the set of control parameters includes one or more of a pulse frequency, a pulse amplitude, a pulse duration, a pulse interval, and a pulse number.

12. The method according to claim 8, wherein after step (d) a given set of control parameters is saved in a memory to form a set of saved control parameters, and step (e) is repeated sequentially instructing the energy pulse generator to deliver to the vagus nerve coupling unit control energy pulses (V1, V2) as defined by the set of saved control parameters.

13. The method according to claim 8, wherein step (e) is repeated sequentially N times instructing the energy pulse generator to deliver to the vagus nerve coupling unit one or more control energy pulses (V1, V2) as defined by a given set of control parameters, and the laryngeal electrical activity (L1, L2) recorded by the laryngeal electrode unit is averaged over the N repetitions of step (g), wherein N is a natural number greater than 1.

14. The method according to claim 8, wherein an electrocardiogram of the patient is measured and the delivery to the vagus nerve coupling unit of one or more control energy pulses is synchronized such that a time, tlx, at which the laryngeal electrical activity (L1, L2) is expected corresponds to an isoelectric period of a cardiac cycle of the patient.

* * * * *